(12) United States Patent
Wirth et al.

(10) Patent No.: US 11,666,300 B2
(45) Date of Patent: Jun. 6, 2023

(54) METHOD FOR THE REAL-TIME CONTROL OF EXPOSURE TO AN X-RAY DOSE

(71) Applicant: TRIXELL, Moirans (FR)

(72) Inventors: Thibaut Wirth, Moirans (FR); Benoit Charles, Moirans (FR)

(73) Assignee: TRIXELL, Moirans (FR)

( * ) Notice: Subject to any disclaimer, the term of this patent is extended or adjusted under 35 U.S.C. 154(b) by 22 days.

(21) Appl. No.: 17/497,405

(22) Filed: Oct. 8, 2021

(65) Prior Publication Data
US 2022/0117573 A1    Apr. 21, 2022

(30) Foreign Application Priority Data

Oct. 15, 2020   (FR) ...................................... 2010567

(51) Int. Cl.
*A61B 6/00*    (2006.01)
*G01T 1/17*    (2006.01)

(52) U.S. Cl.
CPC ............ *A61B 6/542* (2013.01); *A61B 6/4233* (2013.01); *A61B 6/56* (2013.01); *G01T 1/17* (2013.01)

(58) Field of Classification Search
CPC ......... A61B 6/4233; A61B 6/542; A61B 6/56; G01T 1/17
See application file for complete search history.

(56) References Cited

U.S. PATENT DOCUMENTS

| | | | |
|---|---|---|---|
| 5,194,736 A | 3/1993 | Meulenbrugge et al. | |
| 5,381,458 A * | 1/1995 | Deslattes ................. | G01T 1/36 378/207 |
| 5,684,888 A * | 11/1997 | Vuylsteke ............. | G06T 7/0002 382/172 |
| 2004/0146189 A1* | 7/2004 | Langan ................ | H04N 5/2176 382/128 |
| 2009/0129659 A1* | 5/2009 | Deutschmann ........ | H04N 5/361 250/252.1 |
| 2012/0199750 A1* | 8/2012 | Kondou ............... | H04N 5/3653 250/370.09 |
| 2013/0121464 A1* | 5/2013 | Tajima ................... | A61B 6/548 378/97 |

(Continued)

FOREIGN PATENT DOCUMENTS

| | | |
|---|---|---|
| EP | 1 001 665 A2 | 5/2000 |
| JP | 5481053 B2 | 4/2014 |

*Primary Examiner* — Blake C Riddick
(74) *Attorney, Agent, or Firm* — BakerHostetler

(57) ABSTRACT

A method for the real-time control of exposure to an X-ray dose emitted by a generator tube for generating an X-ray beam and received by a detector includes a flat panel detector, comprising a set of pixels organized into a matrix along rows and columns and configured so as to generate signals on the basis of the X-ray dose impinging on the detector, the generator tube comprising a control unit for controlling the generator tube that is configured so as to control an emitted X-ray dose, the control method comprising the following steps: exposing the flat panel detector to an X-ray dose emitted by the generator tube for generating an X-ray beam; repeatedly reading out at least one of the rows of pixels while the flat panel detector is exposed to the X-ray dose; determining a payload signal and a stray signal based on the signals from the readout of the at least one of the rows; transmitting the payload signal to the control unit for controlling the generator tube.

5 Claims, 4 Drawing Sheets

(56) References Cited

U.S. PATENT DOCUMENTS

| | | | | |
|---|---|---|---|---|
| 2013/0148782 A1* | 6/2013 | Tajima | ............. | A61B 6/548 |
| | | | | 378/62 |
| 2013/0202086 A1* | 8/2013 | Tsuji | ............. | H01L 27/14605 |
| | | | | 378/62 |
| 2014/0205066 A1* | 7/2014 | Kitagawa | ............. | A61B 6/542 |
| | | | | 378/62 |
| 2015/0078528 A1* | 3/2015 | Okada | ............. | G01T 1/15 |
| | | | | 378/97 |
| 2015/0131785 A1* | 5/2015 | Topfer | ............. | H04N 5/32 |
| | | | | 378/98 |
| 2017/0079610 A1* | 3/2017 | Morf | ............. | A61B 6/4233 |
| 2018/0098746 A1* | 4/2018 | Kato | ............. | A61B 6/032 |
| 2018/0299565 A1* | 10/2018 | Cresens | ............. | H05G 1/265 |
| 2021/0121151 A1* | 4/2021 | Boutry | ............. | A61B 6/5282 |

* cited by examiner

METHOD FOR THE REAL-TIME CONTROL OF EXPOSURE TO AN X-RAY DOSE

CROSS-REFERENCE TO RELATED APPLICATIONS

This application claims priority to foreign French patent application No. FR 2010567, filed on Oct. 15, 2020, the disclosure of which is incorporated by reference in its entirety.

FIELD OF THE INVENTION

The invention lies in the technical field of radiography with a digital flat panel detector, and more particularly devices for the real-time control of exposure levels.

BACKGROUND

Exposure parameters (voltage, current, source/patient/detector distances) have to be adjusted in order to minimize the dose received by the patient while still guaranteeing an optimum image quality for the radiologist. The optimum exposure parameters depend on the build of the patient, on the type of examination required and the sensitivity features of the X-ray imager (silver film, PSP plate, digital flat panel detector, etc.). These parameters are generally determined using system software, based on indications about the context of the examination (build of the patient, type of image required) as supplied by the radio operator. If these parameters are defined incorrectly, either due to incorrect or inaccurate indications or due to incorrect calibration of the system, there is a significant risk of the image being overexposed or underexposed. These risks involve the risk of overexposing the patient to X-rays, either directly or because the image has to be taken again.

FIG. 1 schematically shows a traditional radiological assembly 50. A radiology assembly 50 consists of two elements: a generator tube 20 for generating an X-ray beam 22 and a flat panel detector 11 for radiographic images. The assembly is intended primarily to take radiographic images of patients in a hospital environment. A patient for whom it is desired to take a radiograph of an area of interest 40 is placed between the generator tube 20 for generating an X-ray beam 22 and the flat panel detector 11. The two elements therefore have to be positioned correctly with respect to one another, such that all of the X-rays emitted by the generator tube 20 for generating the X-ray beam are captured by the flat panel detector 11. Reference is then made to correct alignment between the two elements. The alignment should be performed before the X-rays are emitted by the generator tube 20 for generating the X-ray beam. The aim is to avoid over-irradiating the patient with X-rays arriving outside the detector. There are several known ways of aligning two elements.

In addition to correctly aligning the X-ray beam with the flat panel detector, it is important to control the exposure parameters so as to ensure that a sufficient X-ray dose has been transmitted in order to guarantee a good image but that the patient has not been over-irradiated.

Until now, the problem of quantifying the exposure dose has been solved in practice using one or the other of the following solutions:

External AEC (abbreviation for the acronym Automatic Exposure Control) device, such as an "ionization chamber" or "solid-state detector". This is a functional unit for automatic dose control (for example an ionization chamber), based on an "X-ray detector+current amplifier" hardware unit separate from the imager and connected to the control unit for controlling the X-ray generator. The detector is placed upstream of the imager and absorbs a very low fraction of the X-rays so as not to interfere with the image. The detector is divided into areas of interest (in general 3 or 5 areas), and is able to supply an electric current for each area to the amplifier. The amplifier is connected on one side to the detector and on the other side to the control unit for controlling the X-ray generator. The function of the amplifier is to supply the generator with a signal, without a delay, corresponding to the updated total exposure level. This signal allows the control unit for controlling the generator to interrupt the emission of X-rays (the stop levels are calibrated when the system is installed).

Internal AEC (Automatic Exposure Control) device, generally involving using the signal received on part of the image. There are two main types of solution. In a first type of solution, the matrix of pixels is physically modified such that an electrical signal specifically dedicated to measuring the signal is routed firstly to a charge-to-voltage converter and then to an analogue-to-digital converter. In a second type of solution (disclosed for example in document JP5481053), the matrix is not modified a priori, but there is no mention of the problem of stray signals from all of the illuminated pixels that are not in the area of interest defined for regulating the exposure.

What is known as a "Preshot" device performing a preliminary exposure with a very low dose. A "pre-image" of the patient is taken at a very low dose just before the "actual image". No real-time signal is supplied to the system, but the final parameters are determined and put in place automatically by the system using a pre-image analysis algorithm.

The external AEC solution has three main drawbacks. It generally incorporates a detector that absorbs X-rays upstream of the imager, this leading to an increased dose on the patient of the order of a few percent. In some cases, the external detector may be downstream of the imager, thereby distorting the information about the quality of the beam seen by the imager, and therefore requiring sophisticated calibration. This AEC solution is furthermore applicable only to fixed systems due to its bulk: the detector needs to be fastened to the imager, and a cable is required to route the signal to the amplifier. It is therefore not applicable to mobile radiography systems or to the capturing of images on a portable detector outside of its dedicated housing. Finally, integrating the system is financially expensive: for a typical room with a table and a support arm, it is necessary to have two AEC units, each of which costs at least 500 euros.

The internal AEC solution has the following drawbacks. It is necessary to modify the matrix of pixels, thereby not allowing the solution to be implemented on pre-existing products. Although proposed in the literature, it is difficult to implement due to the technical problem of capacitive coupling between illuminated pixels and the AEC signal readout column.

What is known as the Preshot solution also has two main drawbacks. It requires the system to be calibrated perfectly, that is to say establishment of a correlation between the parameters for a small dose (pre-image) and the parameters for a normal dose (image). This correlation also has to take into account the context of the examination (build of the patient, type of image required). It also assumes a delay time between the pre-image and the image, which may degrade the application flow: waiting time, effect of the patient moving, etc.

SUMMARY OF THE INVENTION

The invention aims to overcome all or some of the problems cited above by proposing a method for the real-time control of exposure to an X-ray dose that makes it possible to indicate to the system, in real time, the greyscale level in the image currently being formed in the imager (digital flat panel detector, hereinafter denoted detector) for a predetermined area of interest of the image in order to guarantee the correct exposure level for the patient. This method is based on directly using the panel of the detector without any modification for the real-time analysis of the signal level in the areas of interest of the image. The method according to the invention moreover proposes an algorithm-based method for solving the significant problem of coupling between the signal of interest (also called payload signal) and the stray signal originating notably from areas illuminated without collimation. Finally, the method according to the invention may be implemented without a wired connection, thereby allowing it to be implemented on a mobile radiography system or in portable cassette mode in a radiography room.

To this end, one subject of the invention is a method for the real-time control of exposure to an X-ray dose emitted by a generator tube for generating an X-ray beam and received by a detector comprising a flat panel detector, the generator tube comprising a control unit for controlling the generator tube that is configured so as to control an X-ray dose emitted by the generator tube, said flat panel detector comprising
  a. a set of pixels organized into a matrix along rows and columns and configured so as to generate signals on the basis of the X-ray dose impinging on the detector;
  b. a circuit configured so as to determine a payload signal based on the signals from at least one of the rows;
  c. a transmission module for transmitting the payload signal to the control unit for controlling the generator tube;
said control method being characterized in that it comprises the following steps:
  exposing the flat panel detector to an X-ray dose emitted by the generator tube for generating an X-ray beam;
  repeatedly reading out at least one of the rows of pixels while the flat panel detector is exposed to the X-ray dose;
  determining a payload signal and a stray signal based on the signals from the readout of the at least one of the rows;
  transmitting the payload signal to the control unit for controlling the generator tube.

Advantageously, the exposure control method according to the invention furthermore comprises a step of adapting the X-ray dose emitted by the generator tube on the basis of the payload signal transmitted to the control unit for controlling the generator tube.

Advantageously, the step of repeatedly reading out at least one of the rows of pixels comprises, for each row of the at least one of the rows, the following steps:
  reading out the column without activation of the row Li in order to obtain a first signal An;
  reading out the column with activation of the row Li in order to obtain a second signal Bn.
Advantageously, the step of determining a payload signal and a stray signal comprises the following steps:

Estimating a multiplication factor (FM') between the payload signal and the stray signal;
Estimating the payload signal based on the multiplication factor using the relationship:

$$DS'_n = (A_n + B_n)/(FM'+1), \text{ and } S'_n = \text{Cumul}(A+B)_n/(FM'+1).$$

Advantageously, the step of estimating the multiplication factor (FM') between the payload signal and the stray signal comprises the following steps:
  based on 3 successive samples of first signals $(A_{n-1}, A_n, A_{n+1}) = (VA)_n$, estimating a measurement $A'_n$ of the stray signal at the time of the second signal $B_n$, (for example through interpolation with the following spline filter: $A'_n = \frac{1}{16} \cdot (-1\ 10\ 7) \cdot {}^t(VA)_n$)
  linear regression on 3 successive points $\{(x_i, y_i); i=1 \text{ to } 3\}$ in order to obtain a proportionality coefficient FP, where:

$$\{x_i\} = [\text{Cumul}(A+B)_{n-2}, \text{Cumul}(A+B)_{n-1}, \text{Cumul}(A+B)_n]$$

$$\{y_i\} = [\text{Cumul}(B-A')_{n-2}, \text{Cumul}(B-A')_{n-1}, \text{Cumul}(B-A')_n]$$

$\text{Cumul}(A)_n$ being equal to $A_0 + A_1 + \ldots + A_n$

Calculating the multiplication factor using the relationship $FM' = (FP)^{-1} - 1$.

In one embodiment, the step of transmitting the payload signal to the control unit for controlling the generator tube is performed through wired transmission.

In another embodiment, the step of transmitting the payload signal to the control unit for controlling the generator tube is performed through wireless transmission, preferably through RF transmission.

The invention also relates to a radiology assembly comprising:
  a. a generator tube for generating an X-ray beam, the generator tube comprising a control unit for controlling the generator tube that is configured so as to control an X-ray dose emitted by the generator tube;
  b. a detector comprising a flat panel detector, said flat panel detector comprising:
    i. a set of pixels (P(i,j)) organized into a matrix along rows (Li) and columns (Cj) and configured so as to generate signals on the basis of the X-ray dose impinging on the detector;
    ii. a circuit configured so as to determine a payload signal based on the signals from some of the rows (Li);
    iii. a transmission module for transmitting the payload signal to the control unit for controlling the generator tube.

In one embodiment, the transmission module for transmitting the payload signal to the control unit for controlling the generator tube is a wired transmission module.

In another embodiment, the transmission module for transmitting the payload signal to the control unit for controlling the generator tube is a wireless transmission module, preferably an RF transmission module.

BRIEF DESCRIPTION OF THE DRAWINGS

The invention will be better understood and further advantages will become apparent from reading the detailed description of one embodiment provided by way of example, which description is illustrated by the attached drawing, in which.

For the sake of clarity, these figures are not all to the same scale. Moreover, the same elements will bear the same references in the various figures.

DETAILED DESCRIPTION

Generally speaking, the invention mentions a traditional image detector typically comprising a flat panel detector comprising a set of pixels organized into a matrix along rows and columns, row addressing units, column readout units, row conductors connecting the rows of pixels to a row addressing unit, and column conductors connecting the columns of pixels to a column readout unit. It should be noted that, in the context of the present patent application, the concepts of column and row have only a relative meaning, with a row of pixels and a column of pixels being nothing more than rows of pixels that are arranged for example, and without limitation, perpendicularly to one another. A row conductor, respectively column conductor, is defined as being oriented parallel to a row of pixels, respectively a column of pixels.

Figure 1:
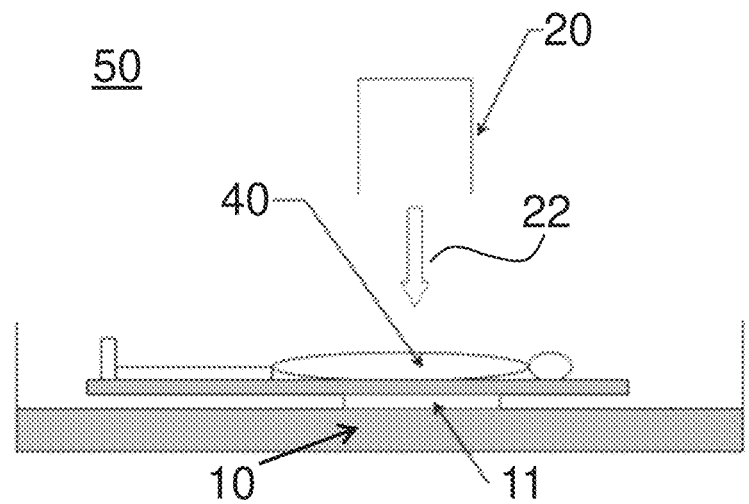
FIG. 1 schematically shows a traditional radiological assembly.

FIG. 1 schematically shows a traditional radiological assembly 50 that has already been presented in the introduction.

Figure 2:
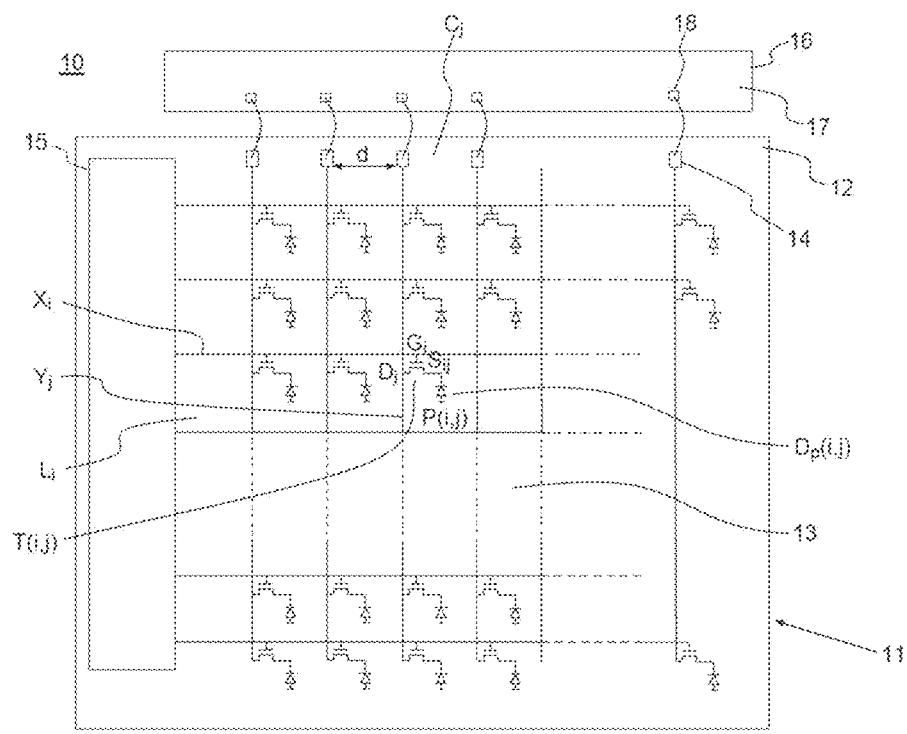
FIG. 2 shows a traditional image detector.

FIG. 2 shows a traditional image detector 10. The image detector 10 comprises a detector 11 formed on a first monolithic substrate 12. The first monolithic substrate 12 comprises a set of pixels P(i,j) organized into a matrix 13 along rows Li and columns Cj. The matrix 13 may contain any number of rows and columns thus forming pixels P(i,j). The matrix 13 forms a geographical area on the first substrate 12. The pixels are denoted in the generic form P(i,j), where i and j are natural integers denoting the rank of the row and the rank of the column in the matrix 13, respectively. The set of pixels P(i,j) is configured so as to generate signals on the basis of radiation impinging on the detector 10. The detector 11 comprises column conductors Yj, each connecting the pixels of a given column Cj. The column conductors Yj are intended to transport the signals generated by the pixels P(i,j). Likewise, the detector 11 comprises row conductors Xi, each connecting the pixels of a given row Li. The matrix 13 of pixels P(i,j) contains columns Cj of even ranks and of odd ranks. Likewise, the matrix 13 of pixels P(i,j) contains rows Li of even ranks and of odd ranks. The detector 10 comprises contact pads 14 located at the edge of the first substrate 12 and outside of the matrix 13 of pixels P(i,j). The contact pads 14 are connected to the column conductors Yj. The image detector 10 comprises a row addressing unit 15 located close to the first substrate 12 and connected to the row conductors Xi. Row addressing unit 15 is the name given to any assembly comprising at least one row addressing unit. The unit 15 may be integrated into the first substrate 12, as shown in FIG. 1, or else integrated into a different substrate. The row addressing unit 15 makes it possible to address each row of pixels Li individually. The image detector 10 comprises a column readout unit 16 formed on a second substrate 17 different from the first substrate 12. The column readout unit 16 comprises connection points 18 that connect the column readout unit 16 to the contact pads 14. The column readout unit 16 makes it possible to read out the signals generated by the pixels of the row selected by the row addressing unit.

A pixel P(i,j) comprises a photodiode Dp(i,j) associated with an electronic switch T(i,j). The photodiodes Dp(i,j) may of course be replaced with any photosensitive element able to generate an electrical signal when it is subjected to photon radiation. The pixel structure shown in FIG. 2 is intentionally simplified, and more complex structures may be implemented within the scope of the invention.

The switch T(i,j) formed by a transistor is connected by its gate Gi to the row conductor Xi of the row i, by its drain Dj to the column conductor Yj and by its source Sij to the cathode of the photodiode Dp(i,j). The anodes of all of the photodiodes Dp(i,j) are connected to a common potential, for example ground. The row addressing unit 15 comprises elements for generating the signals to be injected onto the row conductors Xi in order to drive the opening and closing of the transistors T(i,j). The column readout unit 16 may comprise elements for processing the signals received on the column conductors Yj. These may in particular be an amplifier and/or an analogue-to-digital converter.

The image detector 11 traditionally operates as follows. In an image capturing phase, the exposure of the photodiodes Dp(i,j) to radiation generates electric charge at the source Sij. The amount of charge at each source Sij depends on the intensity of the radiation received by the pixel P(i,j) under consideration. The image capturing phase is followed by a readout phase, performed row by row. The signals injected onto the various row conductors Xi move successively to the active state, such that the potential of each column conductor Yj is successively representative of the amount of electric charge accumulated in the various pixels P(i,j) of the column j.

As explained above, quantifying the exposure dose in the prior art requires modifying the matrix of pixels. And even if the matrix is not modified, the prior art does not propose any solution for eliminating the inevitable stray signal.

Figure 3:
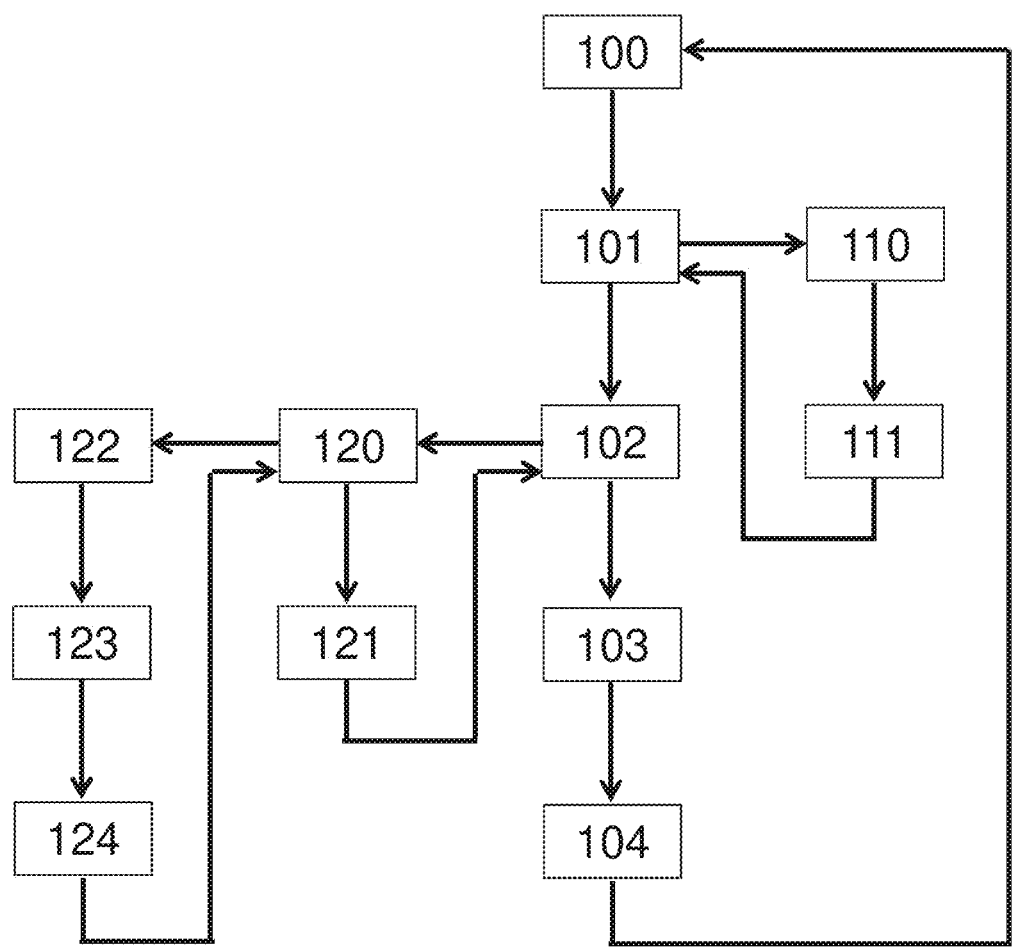
FIG. 3 shows a diagram of the steps of the method for the real-time control of exposure to an X-ray dose according to the invention.

FIG. 3 shows a diagram of the steps of the method for the real-time control of exposure to an X-ray dose according to the invention. To better understand the elements, reference may be made to FIG. 2, in so far as the proposed solution does not require modifying the matrix of pixels.

The invention relates to a method for the real-time control of exposure to an X-ray dose 22 emitted by a generator tube 20 for generating an X-ray beam and received by a detector 10. The detector 10 comprises a flat panel detector 11, and the generator tube 20 comprises a control unit 21 for controlling the generator tube 20, configured so as to control an X-ray dose emitted by the generator tube 20. The flat panel detector 11 comprises:

a set of pixels P(i,j) organized into a matrix 13 along rows Li and columns Cj and configured so as to generate signals on the basis of the X-ray dose 22 impinging on the detector 10;

a circuit 30 configured so as to determine a payload signal based on the signals from at least one of the rows Li;

a transmission module 31 for transmitting the payload signal to the control unit for controlling the generator tube 20.

The circuit 30 is preferably an integrated circuit. However, other equivalent variants may be used. In other words, any device for determining a payload signal based on the signals from one of the rows Li is suitable.

According to the invention, the control method comprises the following steps:

- exposing (step 100) the flat panel detector 11 to an X-ray dose 22 emitted by the generator tube 20 for generating an X-ray beam;
- repeatedly reading out (step 101) at least one of the rows Li of pixels P(i,j) while the flat panel detector 11 is exposed to the X-ray dose 22;
- determining (step 102) a payload signal and a stray signal based on the signals from the readout of the at least one of the rows Li;
- transmitting (step 103) the payload signal to the control unit 21 for controlling the generator tube 20.

Step 101 of repeatedly reading out at least one of the rows Li of pixels P(i,j) of the matrix 13 takes place during exposure step 100. In other words, this readout step takes place at a time when no row Li is traditionally read out in the prior art. Specifically, in conventional mode, the detector 10 does not do anything during the exposure phase.

It may furthermore be noted that readout step 101 is performed on one or more rows Li of the matrix of pixels. These rows are present and contribute to the normal operation of the detector. In other words, there is no need to modify the matrix of pixels in order to implement this specific step of reading out rows during the exposure to X-rays.

In order to obtain a fastest possible readout step 101, it is possible to open all of the rows provided in this step 101 at the same time, which will have the negative effect of combining all of the areas of interest into a single item of information. It is also possible to activate only the one or more rows corresponding to a predefined area of interest.

Exposing the pixels in exposure step 100 leads to the creation of charge outside the pixels P(i,j), in the column Cj, since capacitive coupling connects each column of the matrix and all of the pixels (transistor and photodiode) attached to this column. The readout of a pixel currently being exposed (step 100) is therefore not representative of the level in the image in the same way as readout after exposure step 100 is finished would be: there is an added stray signal from the charge created in the column through coupling. This stray signal may be significant since, for each column, the coupling stems from all of the illuminated pixels in the column. Since the pixel of interest is generally under the patient, if a large number of other pixels are illuminated without attenuating the direct flux (low collimation), the stray signal may have a value up to one hundred times the payload signal. It is therefore imperative to take this stray signal into account in step 102 of determining the (payload and stray) signals.

To determine the payload signal and the stray signal, step 101 of repeatedly reading out at least one of the rows Li of pixels comprises, for each row Li of the at least one of the rows Li, the following steps:

- reading out (step 110) the column Cj without activation of the row Li in order to obtain a first signal $A_n$;
- reading out (step 111) the column Cj with activation of the row Li in order to obtain a second signal $B_n$.

A dual readout is thus performed for each row dedicated to the readout in step 101: the column is firstly read out without activating the row (step 110) in order to obtain a sample $A_n$ for the $n^{th}$ dual readout, and then the column is read out again with activation of the row (step 111) in order to obtain a sample $B_n$ for the $n^{th}$ dual readout. This dual readout makes it possible to subtract the stray effect. These dual readouts are repeated until the end of the window XRW (XRW being the abbreviation for the term X-ray window, that is to say the duration for which the detector is able to receive X photons and to convert them into electric charge before the readout phase). Based on the information obtained by the dual readouts $A_n$ and $B_n$, it will be possible to infer the real signal level in the image.

Simply subtracting ($B_n - A_n$) from the dual readouts does not make it possible to definitively obtain the increase in the payload signal $DS_n$, because the dosage flux is not constant throughout the exposure (step 100). In the initial phase of increasing the dosage flux, the first non-zero readout $A_{n0}$ of the column has a lower level than what it would be if the column were to be read out at the date of the readout $B_{n0}$. In other words, the readout $B_{n0}$ contains more stray signal than $A_{n0}$. The subtraction $B_{n0} - A_{n0}$ therefore contains some stray signal, and overestimates the added payload signal $DS_{n0}$. By contrast, in the event of a flux decrease, for example after having a maximum in the exposure ("overshoot"), the signal Ani is greater than the stray signal contained in $B_{n1}$, and therefore the subtraction $B_{n1} - A_{n1}$ underestimates the variation in the payload signal $DS_{n1}$, or even gives a negative result.

To solve this problem, the solution proposed by the invention takes the hypothesis that the minimum exposure time is slightly below a brief duration, by way of illustration of the order of 1 ms, for example 0.8 ms, and that the constraint according to which an electrical stop signal has to reach the control unit for controlling the generator a small time after, for example less than 0.1 ms after, the effective achievement of a certain signal level in the imager (CP constraint) may be removed below this time. This means that a buffer delay time of 0.8 ms is given for analysis at the start of exposure, and that past this delay time, the constraint (CP) is complied with again. In terms of hazard analysis, this means that the responsibility of not overexposing the patient, which still falls on the radiography system, is based primarily on a choice of non-aberrant parameters during this first delay time of 0.8 ms.

Hereinafter, the main hypothesis (HP), according to which the algorithm has a delay time of 0.8 ms from the start of exposure before having to definitively comply with the constraint (CP), is assumed to be valid.

This delay time (HP) will then be used to robustly estimate a multiplication factor FM' between the payload signal and the stray signal for a current exposure. Specifically, this factor remains constant throughout the exposure, regardless of the temporal profile of the dosage flux, since it is determined entirely by the relative exposure configuration between the pixels of interest of a column and the rest of the pixels of the column (for each column). If multiple columns are joined to increase the signal quality at each readout, the multiplication factor to be applied to this set of columns will also remain constant.

To this end, step 102 of determining a payload signal and a stray signal comprises the following steps:

- Estimating (step 120) a multiplication factor (FM') between the payload signal and the stray signal;
- Estimating (step 121) the payload signal based on the multiplication factor using the relationship:

$$DS'_n = (A_n + B_n)/(FM' + 1), \text{ and } S'_n = \text{Cumul}(A+B)_n/(FM'+1).$$

More precisely, step 120 of estimating the multiplication factor FM' between the payload signal and the stray signal comprises the following steps:

based on 3 successive samples of first signals $(A_{n-1}, A_n, A_{n+1})=(VA)_n$, estimating (step 122) a measurement $A'_n$ of the stray signal at the time of the second signal $B_n$;

linear regression (step 123) on 3 successive points $\{(x_i, y_i); i=1 \text{ to } 3\}$ in order to obtain a proportionality coefficient FP, where:

$$\{x_i\}=[\text{Cumul}(A+B)_{n-2}, \text{Cumul}(A+B)_{n-1}, \text{Cumul}(A+B)_n]$$

$$\{y_i\}=[\text{Cumul}(B-A')_{n-2}, \text{Cumul}(B-A')_{n-1}, \text{Cumul}(B-A')_n]$$

$\text{Cumul}(A)_n$ being equal to $A_0+A_1+\ldots+A_n$

Calculating (step 124) the multiplication factor using the relationship $FM'=(FP)^{-1}-1$.

Step 122 may be performed for example through interpolation with the following spline filter: $A'_n=\frac{1}{16}\cdot(-1\ 10\ 7)\cdot{}^t(VA)_n)$ This estimate is good if the shape of the pulse is approximated well by a polynomial between the 3 measured points, as is commonplace. Other filters were tested, such as for example the arithmetic mean $(0\ 0.5\ 0.5)\cdot{}^t(A)$.

The estimate $A'_n$ corresponds to what the measurement of the stray signal would be at the time of $B_n$.

Linear regression step 123 is justified by the fact that the amount $\text{Cumul}(A+B)_n$ is in principle proportional to the signal level accumulated over time of $B_n$, with a multiplication factor equal to $FM'+1$, which corresponds to the accumulation of the stray signals $(FM'*DS_n)$ and of the payload signals $(1*DS_n)$. The stray signal added to the time of $B_n$ is estimated only by $A'_n$, which may lead, in the event of a sharp variation in the pulse, to a shift in the reproduced signal with respect to the real signal.

The idea of regression on 3 points makes it possible to make up for this shift, provided that there is a less "bumpy" period of the pulse that lasts for the time of a few dual readouts (without the flux otherwise having to remain constant).

The proportionality coefficient FP given by the above linear regression therefore makes it possible to give an estimate FM' of the multiplication factor using the relationship: $FM'+1=(FP)^{-1}$, that is to say $FM'=(FP)^{-1}-1$ If the correlation coefficient CC of the regression is deemed to be close enough to 1 (for example $|1-CC|<10^{-5}$), then it may be considered that FM is estimated robustly by FM'.

If the correlation coefficient CC is not close enough to 1, then steps 122 and 123 are reiterated by changing from n to n+1, while at the same time verifying that the delay time given by the main hypothesis (HP) is not exceeded.

Once the multiplication factor has been estimated with enough confidence, it is possible to give an estimate $DS'_n$ of the level of the payload signal $DS_n$ added at each time of $B_n$ using the formula: $DS'_n=(A_n+B_n)/(FM'+1)$ And this therefore also gives: $S'_n=\text{Cumul}(A+B)_n/(FM'+1)$ This payload signal is transmitted to the control unit for controlling the generator tube.

Finally, the exposure control method according to the invention advantageously comprises a step 104 of adapting the X-ray dose 22 emitted by the generator tube 20 on the basis of the payload signal transmitted to the control unit 21 for controlling the generator tube 20. This therefore guarantees that the patient receives the correct X-ray dose in order to allow a high-quality image to be obtained, without needless overexposure.

The invention gives an algorithm-based solution for correcting the capacitive coupling between pixels and column.

These steps exhibited good results when simulated (FIGS. 2 and 3). The situation is more favourable for a short pulse, since the dosage flux is then high and each sample has a good signal-to-noise ratio. This is good news, since critical situations from the client point of view tend to be those with a short pulse.

On the other hand, for long pulses (tens of ms), the dosage flux may be low and the signal-to-noise ratio deteriorates for each readout. To overcome this problem, besides summing multiple columns (averaging effect), it is proposed for the X-ray window (XRW) duration information, passed to the detector in the frame request, to be used to define a longer readout time increment, while at the same time keeping the objective of having an estimated signal error of less than 10%.

Step 103 of transmitting the payload signal to the control unit for controlling the generator tube may be performed through wired transmission, or through wireless transmission, preferably through RF transmission. Generally speaking, it is necessary to have fast transmission that has a minimum and well-controlled latency time. Wi-Fi and Bluetooth links, although they are applicable in the context of the invention, are therefore less suitable.

The information is advantageously transmitted in real time. The information on the signal level at the time of $B_n$, obtained in step 102, should be transmitted to the control unit 21 for controlling the generator tube 20 with a delay of less than 0.1 ms with respect to the time of $B_n$. Since the algorithm for performing step 102 is implemented in an FPGA integrated circuit, and its principle does not require a large number of calculations, most of this constraint regarding the delay is relevant to step 103 of transmitting the information from the integrated circuit to the control unit. The case of a wired link does not pose any particular problem. The case of an RF wireless link is far more difficult.

If the delay linked to the RF link is greater than 0.1 ms, it is possible to contemplate a step of extrapolating the information supplied in step 102, provided that this is timestamped and the transmitter (transmission module) and receiver (control unit) elements are synchronized beforehand.

Figure 4:
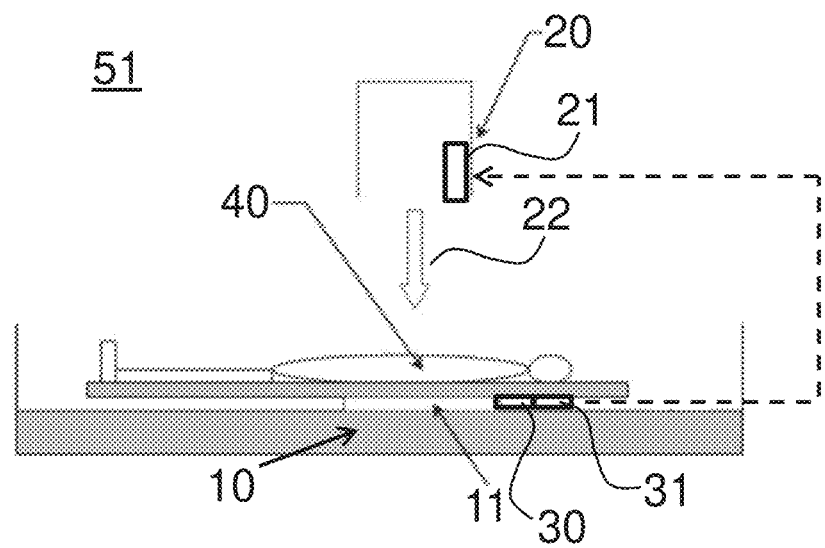
FIG. 4 schematically shows a radiological assembly according to the invention.

FIG. 4 schematically shows a radiological assembly 51 according to the invention. The radiology assembly 51 comprises:

a generator tube 20 for generating an X-ray beam, the generator tube 20 comprising a control unit 21 for controlling the generator tube 20 that is configured so as to control an X-ray dose 22 emitted by the generator tube 20;

a detector 10 comprising a flat panel detector 11, said flat panel detector 11 comprising:

a set of pixels P(i,j) organized into a matrix 13 along rows Li and columns Cj (similar to the detector presented in FIG. 2) and configured so as to generate signals on the basis of the X-ray dose 22 impinging on the detector 10;

a circuit 30 configured so as to determine a payload signal based on the signals from some of the rows Li.

a transmission module 31 for transmitting the payload signal to the control unit 21 for controlling the generator tube 20.

The circuit 30 may be an integrated circuit. The integrated circuit may be any circuit suitable for performing calculations. By way of example and without limitation, it may be an FPGA (abbreviation for "field-programmable gate array", signifying programmable logic arrays). The integrated circuit performs the steps of analysing the data of dedicated rows in order to extract the signal level information at a given time. The information is routed to the control unit for controlling the generator, either directly via a wired link or by way of a radio link (RF option).

The transmission module 31 for transmitting the payload signal to the control unit 21 for controlling the generator tube 20 may be a wired transmission module, or a wireless transmission module, preferably an RF transmission module. It transmits the signal information at a given time to the receiver module of the generator tube. The receiver module receives the signal level information at a given time, converts it into an electrical signal and supplies it to the control unit for controlling the X-ray generator.

Figure 5:
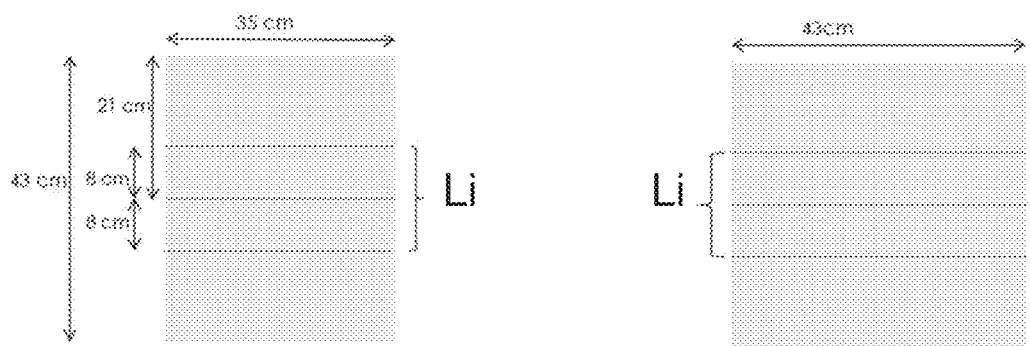
FIG. 5 illustrates the principle of positioning the rows of the matrix of the detector that are dedicated to the readout, and the repeated readout according to the invention.
Figure 5:
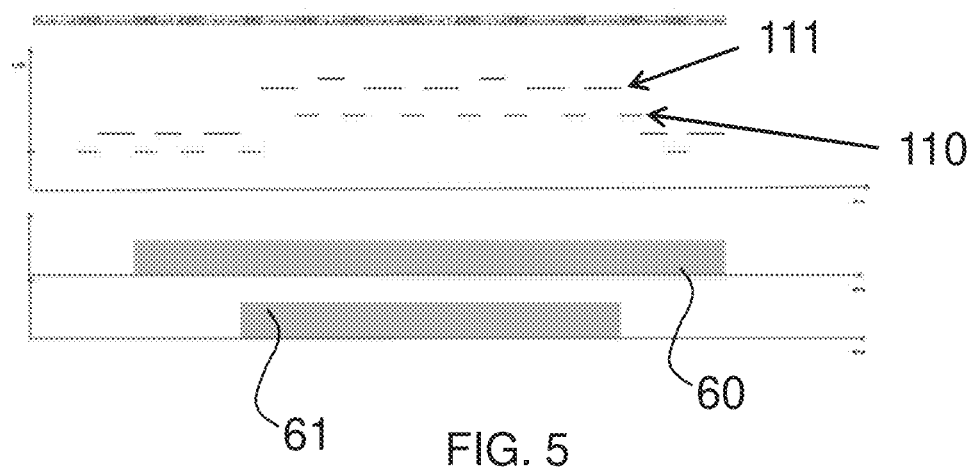

FIG. 5 illustrates the principle of positioning the rows of the matrix of the detector that are dedicated to the readout and the repeated readout according to the invention. Only the rows involved in repeated readout step 101 are shown (upper part of the figure). These are existing rows that are already present in the matrix of the detector. The measurements are given by way of indication in order to show possible exemplary embodiments. In this figure, three rows are used for step 101. There could be just one row, or else two, or even more. These rows are read out continuously, as quickly as possible during the X-ray window 60 (reference 61 represents the X-ray emission window). To ascertain a representative value, at least the readout of the column without activating the row (step 110) and the readout of the column with activation of the row are mandatory. This means that, during the X-ray window, step 110 and then step 111 are performed alternately (that is to say the columns with the activated rows are read out).

Figure 6:
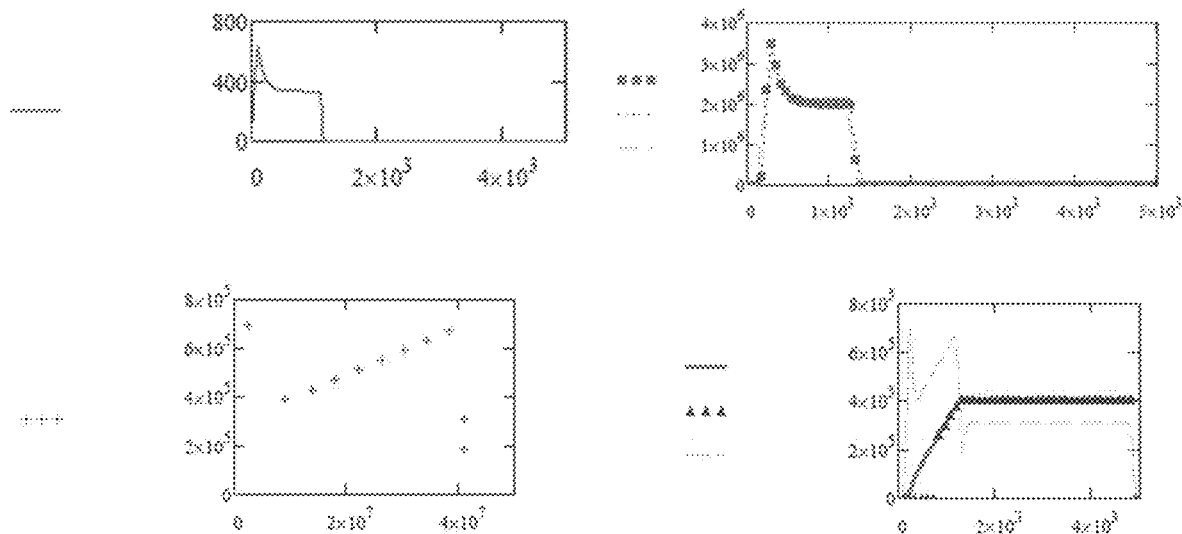
FIG. 6 shows the results of a simulation of an exposure with a fast rise in the implementation of the method according to the invention.

FIG. 6 shows the results of a simulation of an exposure with a fast rise in the implementation of the method according to the invention.

Figure 7:
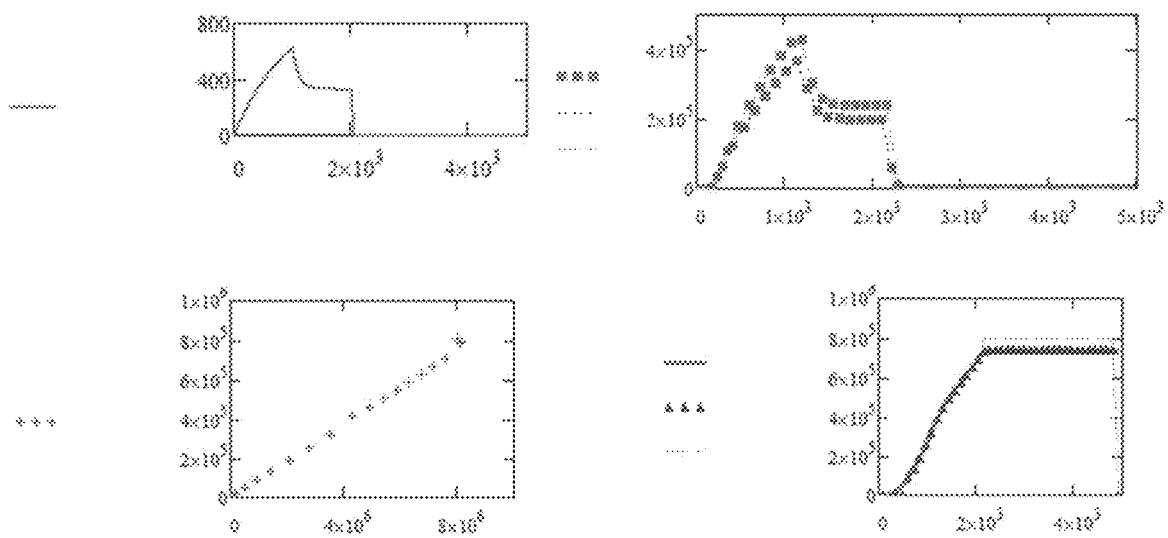
FIG. 7 shows the results of a simulation of an exposure with a slow rise in the implementation of the method according to the invention.

FIG. 7 shows the results of a simulation of an exposure with a slow rise in the implementation of the method according to the invention.

For these two figures, it is possible to see the shape of the simulated pulse at the top right. The graph of Cumul$(B-A')_n$ as a function of Cumul$(A+B)_n$ is shown at the bottom left. It is possible to see the verification of the operation of the estimate as a function of elapsed time at the bottom right: actual payload signal (represented in an unbroken line), payload signal estimated using Cumul$(A+B)_n/(FM'+1)$ (represented by triangles), which is non-zero as long as CC is close enough to 1, and what the estimate Cumul$(B-A')_n$ would be (represented in dashed lines).

In FIG. 6, the samples $A_n$ and $B_n$ are simulated with a multiplication factor FM=100. It is seen that the linear regression may work as early as the $2^{nd}$ triplet of points.

In FIG. 7, the samples $A_n$ and $B_n$ are simulated with a multiplication factor FM=10.

These two figures demonstrate the effectiveness of the proposed solution for the capacitive coupling problem.

The invention proposes a method for real-time exposure control with the advantages of being able to implement it without any physical modification or specific adjustment of the matrix of photodiodes (fast readout of existing dedicated rows of the panel during exposure). The signal level in the areas of interest of the image is analysed in real time. Step 102 makes it possible to solve the significant problem of coupling between the signal of interest and the stray signal originating notably from areas illuminated without collimation.

Finally, this method is compatible with transmission without a wired connection, extending the possibilities of use to mobile radiography or in portable cassette mode in a radiography room.

The proposed solution gives a signal level in real time. It consists in directly using the panel of the detector without any modification for the real-time analysis of the signal level in the areas of interest of the image. Moreover, the proposed solution describes an algorithm-based method for solving the significant problem of coupling between the signal of interest and the stray signal originating notably from areas illuminated without collimation. Finally, the proposed solution may be implemented without a wired connection, thereby allowing implementation on a mobile radiography system or in portable cassette mode in a radiography room.

The invention claimed is:

1. A method for the real-time control of exposure to an X-ray dose emitted by a generator tube for generating an X-ray beam and received by a detector comprising a flat panel detector, the generator tube comprising a control unit for controlling the generator tube that is configured so as to control an X-ray dose emitted by the generator tube, said flat panel detector comprising:
   a. a set of pixels (P(i,j)) organized into a matrix along rows (Li) and columns (Cj) and configured so as to generate signals on the basis of the X-ray dose impinging on the detector;
   b. a circuit configured so as to determine a payload signal based on the signals from at least one of the rows (Li);
   c. a transmission module for transmitting the payload signal to the control unit for controlling the generator tube;
   said control method comprising the following steps:
      exposing the flat panel detector to an X-ray dose emitted by the generator tube for generating an X-ray beam;
      repeatedly reading out at least one of the rows (Li) of pixels (P(i,j)) while the flat panel detector is exposed to the X-ray dose;
      determining a payload signal and a stray signal based on the signals from the readout of the at least one of the rows (Li);
      transmitting the payload signal to the control unit for controlling the generator tube;
   said control method being wherein the step of repeatedly reading out at least one of the rows (Li) of pixels comprises, for each row (Li) of the at least one of the rows (Li), the following steps:
      reading out the column (Cj) without activation of the row (Li) in order to obtain a first signal (An);
      reading out the column (Cj) with activation of the row (Li) in order to obtain a second signal ($B_n$);
   in that the step of determining a payload signal and a stray signal comprises the following steps:
      estimating a multiplication factor (FM') between the payload signal and the stray signal;
      estimating the payload signal based on the multiplication factor using the relationship:

$$DS'_n = (A_n + B_n)/(FM'+1), \text{ and } S'_n = \text{Cumul}(A+B)_n/(FM'+1).$$

where $DS'_n$ is a level of the payload signal, $S'_n$ is the payload signal, and Cumul $(A+B)_n$ is a signal level accumulated over time of $B_n$;
   and the step of estimating the multiplication factor (FM') between the payload signal and the stray signal comprises the following steps:

based on 3 successive samples of first signals $(A_{n-1}, A_n, A_{n+1}) = (VA)_n$, estimating a measurement $A'_n$ of the stray signal at the time of the second signal $B_n$;

linear regression on 3 successive points $\{(x_i, y_i); i=1 \text{ to } 3\}$ in order to obtain a proportionality coefficient (FP), where:

$\{x_i\} = [\text{Cumul}(A+B)_{n-2}, \text{Cumul}(A+B)_{n-1}, \text{Cumul}(A+B)_n]$, $\{y_i\} = [\text{Cumul}(B-A')_{n-2}, \text{Cumul}(B-A')_{n-1}, \text{Cumul}(B-A')_n]$, and $\text{Cumul}(A)_n = A_0 + A_1 + \ldots + A_n$;

calculating the multiplication factor using the relationship $FM' = (FP)^{-1} - 1$.

2. The method for the control of exposure according to claim 1, furthermore comprising a step of adapting the X-ray dose emitted by the generator tube on the basis of the payload signal transmitted to the control unit for controlling the generator tube.

3. The method for the control of exposure according to claim 1, wherein the step of transmitting the payload signal to the control unit for controlling the generator tube is performed through wired transmission.

4. The method for the control of exposure according to claim 1, wherein the step of transmitting the payload signal to the control unit for controlling the generator tube is performed through wireless transmission.

5. The method for the control of exposure according to claim 4, wherein the wireless transmission is RF transmission.

\* \* \* \* \*